(12) United States Patent
Li et al.

(10) Patent No.: US 10,408,720 B1
(45) Date of Patent: Sep. 10, 2019

(54) TESTING APPARATUS FOR DETERMINING TENSILE STRENGTH OF SOFT ROCK AND SOIL

(71) Applicant: Taiyuan University of Technology, Taiyuan, Shanxi (CN)

(72) Inventors: Yanrong Li, Shanxi (CN); Bin Li, Shanxi (CN)

(73) Assignee: Taiyuan University of Technology, Taiyuan (CN)

( * ) Notice: Subject to any disclaimer, the term of this patent is extended or adjusted under 35 U.S.C. 154(b) by 0 days.

(21) Appl. No.: 16/377,303

(22) Filed: Apr. 8, 2019

(51) Int. Cl.
*G01N 3/08* (2006.01)

(52) U.S. Cl.
CPC ....... *G01N 3/08* (2013.01); *G01N 2203/0017* (2013.01)

(58) Field of Classification Search
CPC ....................................................... G01N 3/08
USPC .......................................................... 73/826
See application file for complete search history.

(56) References Cited

U.S. PATENT DOCUMENTS 3,379,054 A * 4/1968 Folweiler ................. G01N 3/08
73/772

* cited by examiner

*Primary Examiner* — Tarun Sinha

(57) ABSTRACT

A testing apparatus for determining tensile strength of soft rock and soil tests a sample having a central hole. A drawbar device holds the sample in a central, upright position. The drawbar device has two main parts, namely the left fixed part and the right lateral movable part. A fixed frame connects to the left fixed part and a lateral movable frame connects to the right lateral movable part. The drawbar device has two arms. The sample is positioned on the central pull rod through the hole of the sample. A tension sensor and a displacement sensor detect the tension force and displacement as the sample is pulled apart. A data analysis module calculates a tensile strength based on the tension force and the displacement by the equation: σt=500 αFmax/(R−r)h.

17 Claims, 5 Drawing Sheets

TESTING APPARATUS FOR DETERMINING TENSILE STRENGTH OF SOFT ROCK AND SOIL

CROSS REFERENCE OF RELATED APPLICATIONS

This application claims the benefits of Chinese patent application no. 201810310993.0, filed on Apr. 9, 2018 and entitled DEVICE AND METHOD FOR TESTING THE TENSILE STRENGTH OF SOFT ROCK AND SOIL, which patent application is incorporated by reference herein in its entirety.

FIELD OF THE INVENTION

The present invention relates generally to a testing apparatus for determining tensile strength of soft rock and soil, whereby a sample having a central hole is centrally positioned and fixedly retained on a drawbar device, whereby a fixed frame supports a left fixed arm, and a lateral movable frame supports a right lateral movable arm, with the arms having a hook portion that fits into the central hole of the sample; whereby an electric cylinder and stepper motor drive the lateral movable frame distally from the fixed frame to symmetrically separate the arms, and thereby separate the left half pull rod and the right half pull rod, thereby separate the sample along an axis in opposing directions; whereby a tension sensor and a displacement sensor detect the tension force and displacement of the right lateral movable arm as the sample is pulled apart; whereby a data acquisition module collects tension force and displacement; and whereby a computer program on a data analysis module automatically generates a tension-displacement curve diagram in real time for graphical analysis of the sample, and finally calculate the tensile strength of the sample based on the tension force, and the geometrical parameters of the sample, and by using the equation: $\sigma_t = 500\ \alpha F_{max}/(R-r)h$, wherein $\sigma_t$ is the tensile strength, $\alpha$ is a sample size correction coefficient, $F_{max}$ is the peak tension force, R is the radius of the sample, r is the radius of the inner hole in the sample, and h is the thickness of the sample.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known in the art that tensile strength of soft rock and soils describes the capacity of the tested material to resist tensile stress as generated by external tension loads. At present, the test methods for soil and soft rock are mainly uniaxial tension method, Brazilian splitting method, axial fracturing method and soil beam bending method. Therein, the uniaxial tension method is a direct test method, and the Brazilian splitting method, the axial fracturing method, and the soil beam bending method are indirect test methods.

The uniaxial tension method is the direct application of tension at the two ends of the sample until the sample is broken. The tensile strength is calculated by the peak tension force divided by the area of the fracture section at the time of fracture. With the uniaxial tension method, in the test, the complete process towards failure of the sample can be observed, which can intuitively reflect the mechanical behavior of the sample under tension. But, the uniaxial tension process has difficulties in mounting the sample of soil and soft rock materials. At present, the uniaxial tension test often uses a clamp or a polymer glue to connect and fix the two ends of the cylindrical sample to the device. The fixing clamp is of two semi-circular jaws, and screws are used to buckle and fasten the two jaws so as to fix the two ends of the sample. Because the soil and soft rock are generally weak and brittle, the ends of the sample are easily damaged under pressure when being fixed with fixing clamp or polymer glue. Secondly, it is difficult to center the clamps at the two ends of the sample, so that eccentric force can be easily generated during the test, which affects the test result. Furthermore, the relative displacement between the clamp and the sample is easy to occur in the process of tension, so that it is difficult to measure the true value of the deformation of the sample. With the use of polymer glue to bond the ends of the sample, the internal structure of the ends of the sample is easily damaged, the sample and the device are difficult to be bonded, and it is easy for the sample and the device to get detached in the process of tension.

The indirect test methods assume that the tensile failure of soil or soft rock follows a certain stress-strain relationship, and the tensile strength of the material is indirectly calculated by using a theoretical formula matching the test method. The specification of the Brazilian splitting method requires that the padding strips must be placed symmetrically above and underneath the sample, and requires that both of the contact lines between the two padding strips and the sample should be on the vertical central section of the sample. But, because the padding strips are small in size, it is difficult to meet the above requirements, so that eccentric pressure occurs when pressure is applied. In addition, the padding strips are likely to move in the process of pressure application, which results in failure of the test.

The fracturing effects of the sample in the axial fracturing test are not easy to control, and because it is difficult to center the upper and lower small-sized cylindrical blocks in the center axis of the sample. The sample as needed for the soil beam bending method is relatively large in size and is difficult to prepare, and it is difficult to make sure that the fracture position of the sample occurs along the middle cross section of the sample.

In addition to the aforesaid existing problems, the load in the current tensile strength test methods is generally provided by a universal testing machine, and the related parts such as clamps, padding strips and cylindrical blocks need to be manufactured and customized additionally, so that the entire test system is expensive in price, and bulky in size. The test requires multiple people to cooperate, the operation is complicated with trivial details, and the efficiency is low. The test involves many steps of manual operation, and it is difficult to achieve precise placement of parts, which affects the final results of the test.

SUMMARY

Illustrative embodiments of the disclosure are generally directed to a testing apparatus for determining tensile strength of soft rock and soil. The testing apparatus is provided with a protective case that is supported on stabilizing foot pads. The components and soil sample are inserted for testing under a glass cover that provides protection during testing.

In one embodiment of the testing apparatus, a soft rock sample is centrally positioned and fixedly retained on a drawbar device. A hole is drilled concentrically in the sample for accurate mounting. A fixed frame connects to the left fixed part of the drawbar device which comprise a fixed arm. A lateral movable frame connects to the right lateral movable part of the drawbar device which comprise a lateral movable arm. The arms have hooks that fit into the central pull rod which sits through the hole of the sample. The lateral movable frame drives the right lateral movable part away from the left fixed part, such that the sample is pulled apart in opposite directions. An electric cylinder drives the lateral movable frame. A stepper motor in operable connection with the electric cylinder, and the stepper motor is configured to drive the electric cylinder. The electric cylinder is in operable connection with the lateral movable frame, whereby the lateral movable frame is driven by the electric cylinder and is moving away from the fixed frame.

In some embodiments, the arms include a hook portion that securely fits into the left half pull rod and the right half pull rod of the central pull rod which sits through the hole of the sample. The lateral movable frame drives the right lateral movable part at a constant rate away from the left fixed part, so that the arms symmetrically separate the sample along an axis. The rate of separation and the tension during separation generates tension force and displacement which are used to derive a tensile strength and the tension-displacement curve diagram.

In some embodiments, a tension sensor and a displacement sensor detect and record the tension force and displacement while the sample is positioned on the drawbar device and separated by pull force. A data acquisition module collects the tension force data and displacement data. A computer program programmable on a data analysis module automatically calculates the tensile strength of the sample based on the following equation: $\sigma_t = 500 \, \alpha F_{max}/(R-r)h$. The computer generates a tension-displacement curve diagram in real time for graphical analysis of the sample. The tensile strength and the tension-displacement curve diagram can be stored, exported, and manipulated to better understand the tensile strength of the sample.

In one aspect, a testing apparatus for determining tensile strength of soft rock and soil, comprises:
  a fixed frame and a lateral movable frame;
  the lateral movable frame being disposed in a parallel relationship with the fixed frame, the lateral movable frame being operable to laterally advance distally and proximally in relation to the fixed frame at a constant displacement rate;
  a stepper motor being in operable connection with the electric cylinder, and being able to drive the electric cylinder;
  an electric cylinder being in operable connection with a tension sensor, the tension sensor further being in operable connection with the lateral movable frame, whereby the lateral movable frame being able to be driven by the electric cylinder via the tension sensor at a constant displacement rate;
  a drawbar device having a left fixed part and a right lateral movable part, wherein the right lateral movable part being laterally movable relative to the left fixed part;
  the left fixed part comprising a left fixed pull seat, a left connecting plate, a left fixed arm and a left half pull rod, whereby the connecting plate is positioned at one end of the left fixed pull seat, and the connection plate is for connecting the left fixed part with the fixed frame, whereby the left half pull rod is positioned at the other end of the left fixed pull seat, whereby a fixed arm is pivotably connected with the upper part of the connecting plate by means of pin;
  similarly, the right lateral movable part comprising a right fixed pull seat, a connecting plate, a right lateral movable arm and a right half pull rod, whereby the connecting plate is positioned at one end of the right lateral pull seat, and the connection plate is for connecting the right lateral movable part with the lateral movable frame, whereby the right half pull rod is positioned at the other end of the right lateral pull seat, whereby right lateral movable arm is pivotably connected with the upper part of the connecting plate by means of pin;
  the drawbar device being connected with the fixed frame and the lateral movable frame by means of the connecting plates respectively, and when the left fixed part and the right lateral movable part of the drawbar device are being contact with each other at the half pull rod, the left half pull rod and the right half pull rod are in contact as well, stick to each other and form a central pull rod of the drawbar device, the central pull rod retaining a sample in an upright, concentric position along an axis, the sample being defined by a central hole;
  the left fixed arm having a hook at the other end opposite to the pin, whereby the hook being fitted in a hole of the left half pull rod of the central pull rod which sits in the hole of the sample;
  similarly, the lateral movable arm having a hook at the other end opposite to the pin, whereby the hook being fitted in a hole of the right half pull rod of the central pull rod which sits in the hole of the sample;
  whereby the lateral movable frame drives the right lateral movable part of the drawbar device away from the left fixed part of the drawbar device at the constant displacement rate, therefore the left half pull rod and the right half pull rod symmetrically separate the sample along the axis in opposing directions;
  a tension sensor detecting a tension generating from a lateral movable frame adapter plate which is being connection with the right lateral movable frame which is further being connection with right lateral movable part of the drawbar device while the right lateral movable part moving distally from the left fixed part;
  a displacement sensor detecting a displacement between the left fixed part and the right lateral movable part of the drawbar device while the right lateral movable part moving distally from the left fixed part;
  a data acquisition module collecting tension force data from the tension sensor, and collecting displacement data from the displacement sensor;
  a data analysis module being in operable communication with the data acquisition module, the data analysis module calculating a tensile strength of the sample based on the following factors: a tensile strength constant, a sample size correction coefficient, a peak tension force, a radius of the sample, a radius of the inner hole in the sample, and a thickness of the sample;
  the data analysis module further generating a tension-displacement curve diagram based on the tension force and the displacement; and
  a computer having a display screen graphically displaying the tension force, the displacement, and the tension-displacement curve diagram in real time.

In another aspect, the testing apparatus further comprising a case, wherein the case comprises a glass cover and a plurality of foot pads, the glass cover pivotally articulating downwardly to cover an upper part of the fixed frame and the lateral movable frame.

In another aspect, wherein the lateral movable frame is operatively connected to the tension sensor through a sensor adapter plate.

In another aspect, wherein the lateral movable frame rests on a lateral movable frame adapter plate.

In another aspect, wherein the lateral movable frame slides along at least one guiding groove.

In another aspect, the testing apparatus further comprising a base plate and a backing plate.

In another aspect, the testing apparatus further comprising a clamping groove operable to help retain the fixed arm and the lateral movable arm.

In another aspect, the testing apparatus further comprising a tension signal converter operable to convert an electrical signal of the tension force into a tension digital signal.

In another aspect, the testing apparatus further comprising a displacement signal converter operable to convert an electrical signal of the displacement into a displacement rate digital signal.

In another aspect, wherein the tension signal converter and the displacement signal converter are being mounted on the base plate.

In another aspect, the testing apparatus further comprising a power module.

In another aspect, the testing apparatus further comprising a power switch operatively connected to the power module.

In another aspect, the testing apparatus further comprising a control board and a control board mounting seat supporting the control board.

In another aspect, the testing apparatus further comprising a stepper drive being operatively connected to the stepper motor.

In another aspect, wherein the data analysis module calculates the tensile strength of the sample based on the following equation: $\sigma t = 500\alpha F_{max}/(R-r)h$, wherein $\sigma t$ is the tensile strength, 500 is a tensile strength constant, $\alpha$ is a sample size correction coefficient, $F_{max}$ is a peak tension force, R is a radius of the sample, r is a radius of the inner hole in the sample, and h is a thickness of the sample.

In another aspect, wherein the connecting plates joining the fixed frame and the lateral movable frame, wherein the connecting plates are defined by a plurality of bumps, the bumps being disposed at opposite ends of the connecting plates, the bumps further engaging the fixed frame and the lateral movable frame.

In another aspect, wherein the fixed arm and the lateral movable arm pivotally join the respective frame about at least one pin.

One objective of the present invention is to affix a sample of soft rock or soil on a drawbar device for symmetrical separation at a constant rate to accurately determine the tensile strength of the soft rock or soil.

Another objective is to align the sample symmetrically between the lateral movable frame and the fixed frame, such that the sample centering frame minimizes eccentric forces and rotational torque while being stretched by the drawbar device.

Another objective is to combine the mechanical structure that stretches the sample of soft rock and soil with the computer program that determines the tensile strength.

Yet another objective is to provide a mechanical structure that is light and simple in structure, easy to carry.

Yet another objective is to simplify the experimental operation and improves the experimental efficiency.

Yet another objective is to provide an inexpensive to manufacture testing apparatus for testing tensile strength.

Other apparatus, testing apparatus, methods, features, and advantages will be or become apparent to one with skill in the art upon examination of the following drawings and detailed description. It is intended that all such additional apparatus, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific testing apparatus and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A testing apparatus 100 for determining tensile strength of soft rock and soil is referenced in FIGS. 1-5. The testing apparatus 100, hereafter "testing apparatus 100" is configured to test the tensile strength of a soft rock, soil, clay, mud, semi-solid aggregate of minerals, and other soft geological material. In operation, the testing apparatus 100 is light and compact in structure, requiring minimal extra components to operate; thereby reducing the changes of systematic errors. The testing apparatus 100 is also configured for mounting sample 140 conveniently and is designed for simple operation with high efficiency for testing. Further, the testing apparatus 100 is operable with any soft rock or soil that can be shaped into a cylindrical sample 140 having a central hole drilled therein. The tensile strength value can easily be derived through use of the testing apparatus 100.

Figure 1:
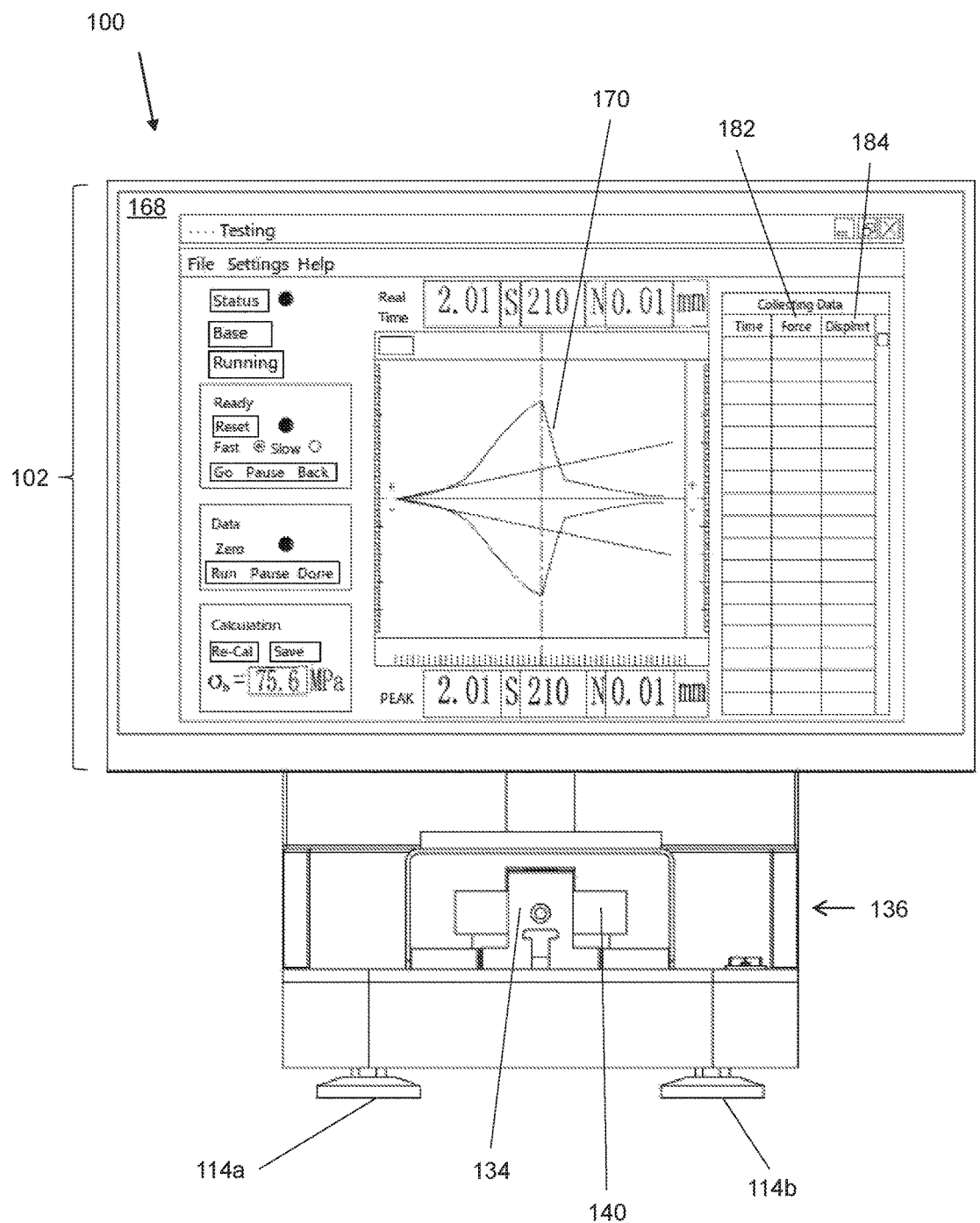
FIG. 1 illustrates a frontal view of an exemplary testing apparatus for determining tensile strength of soft rock and soil, in accordance with an embodiment of the present invention.

Referring to FIG. 1, the testing apparatus 100 provides a protective case 108. The components and soil sample 140 are inserted for testing under a glass cover 136 that provides protection during testing. In one embodiment, the glass cover 136 pivotally articulates downwardly to cover an upper part of a fixed frame 134 and a lateral movable frame 144, described below. The case 108 provides a protective outer housing for protecting the inner components from physical forces, moisture, and debris during testing. In one non-limiting embodiment, the case 108 is supported on four stabilizing foot pads 114a, 114b, which may be height adjustable. Suitable materials for the case 108 may include, without limitation, stainless steel, a rigid polymer, aluminum, titanium, and polyvinyl chloride.

In one embodiment of the testing apparatus 100, a soft rock sample 140 is centrally positioned and fixedly retained on a drawbar device 142. The drawbar device 142 has a central pull rod 166 that is disposed in a vertical position. The central pull rod 166 has two semi-cylinders, namely, a left half pull rod 190 and a right half pull rod 192. When the left half pull rod 190 and the right half pull rod 192 are stick together, they just become the central pull rod 166. The left half pull rod 190 is engaged with the left fixed arm 154 through a left terminal hook at the end of the left fixed arm 154. The right half pull rod 192 is engaged with the right lateral movable arm 160, and can be pulled towards a direction opposite to the left half pull rod 190, along with the drawbar device 142. The central pull rod 166, when the left half pull rod 190 and the right half pull rod 192 are stick together to each other, retains a sample 140 of a soft rock in an upright, concentric position along an axis 172. The central pull rod 166 is also used to standardize the position and posture of the sample to ensure that no deviatoric stress is generated during tension; and therefore the test result is accurate.

In essence, the central pull rod 166 standardizes the position of the sample to ensure that the tensile force is along the same straight line, so that the problem of eccentric force that easily occurs in the direct stretching method, the Brazilian splitting method and the axial fracturing method is avoided. The test results are uniform, the tensile failure sections are all perpendicular to the stretching direction, and appear in the middle position of the sample, so that the test quality is high.

The axis 172 runs through the central hole in the sample 140. In some embodiments, the sample 140 is molded in to a substantially cylindrical shape, and a hole is drilled concentrically in the sample 140 for accurate mounting. The outer radius of the sample 140, and an inner radius of the hole are measured for subsequent tensile strength calculations.

The sample 140 is mounted vertically, and is stable without slip, the central pull rod 166 is used to standardize the sample position, which prevents the generation of deviatory stress and guarantees unification of sample damage effects, so that the test result is accurate and reliable. Those skilled in the art will recognize that quiet testing conditions are important for precise scientific stretch tensile strength tests.

In essence, the sample 140 is pulled apart along the axis 172, by means of pulling the right half pull rod 192 through the right lateral movable arm 160, and the tension and displacement required to separate the sample 140 into two sample pieces is determinative of a tensile strength test value of the sample 140; which can be based on the factors of a tensile strength constant, a sample size correction coefficient, a peak tension force, a radius of the sample, a radius of the inner hole in the sample, and a thickness of the sample.

Figure 2:
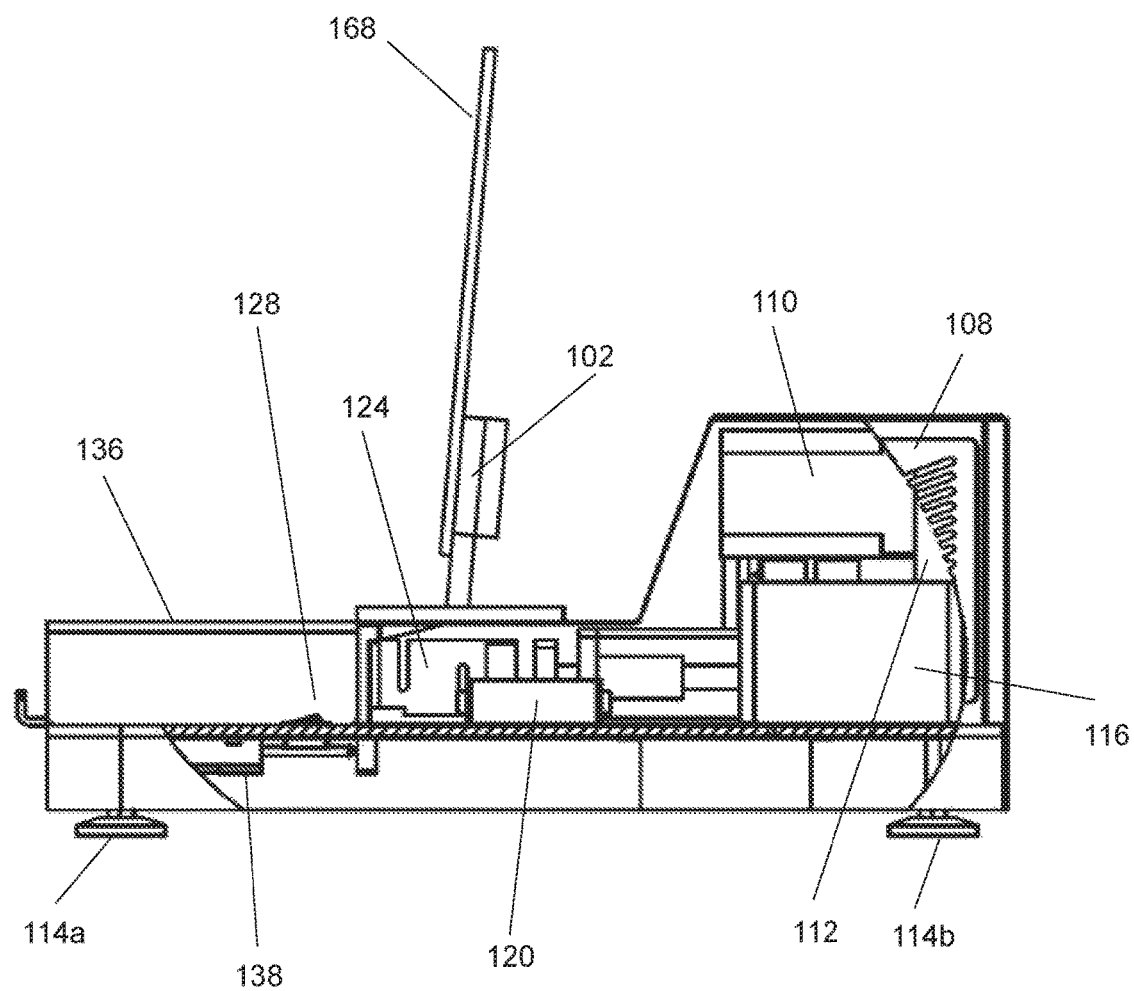
FIG. 2 illustrates a sectioned side view of the testing apparatus shown in FIG. 1, in accordance with an embodiment of the present invention.
Figure 3:
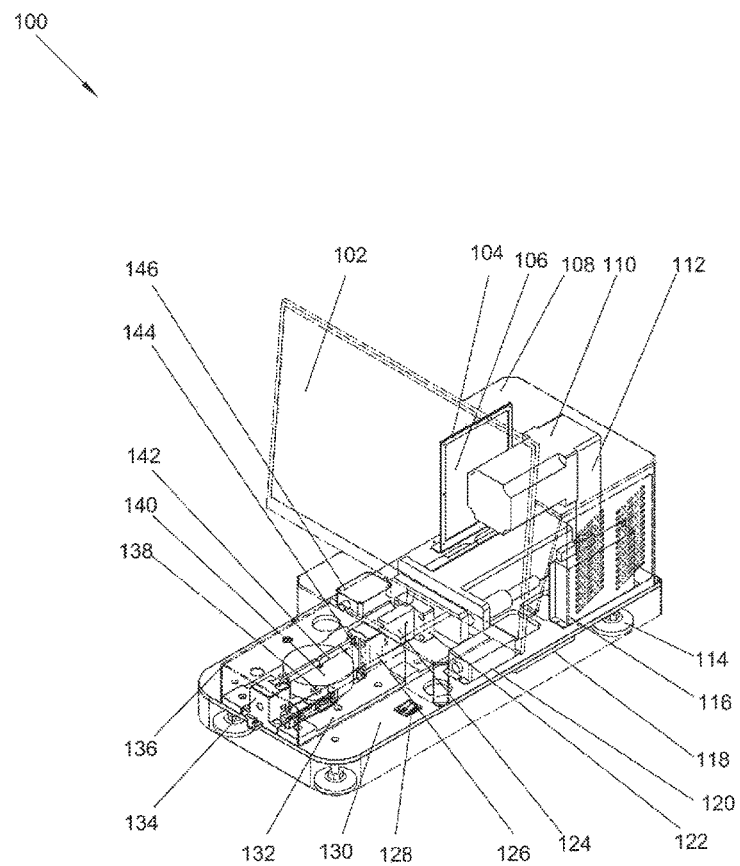
FIG. 3 illustrates a perspective view of the testing apparatus shown in FIG. 1, in accordance with an embodiment of the present invention.
Figure 4:
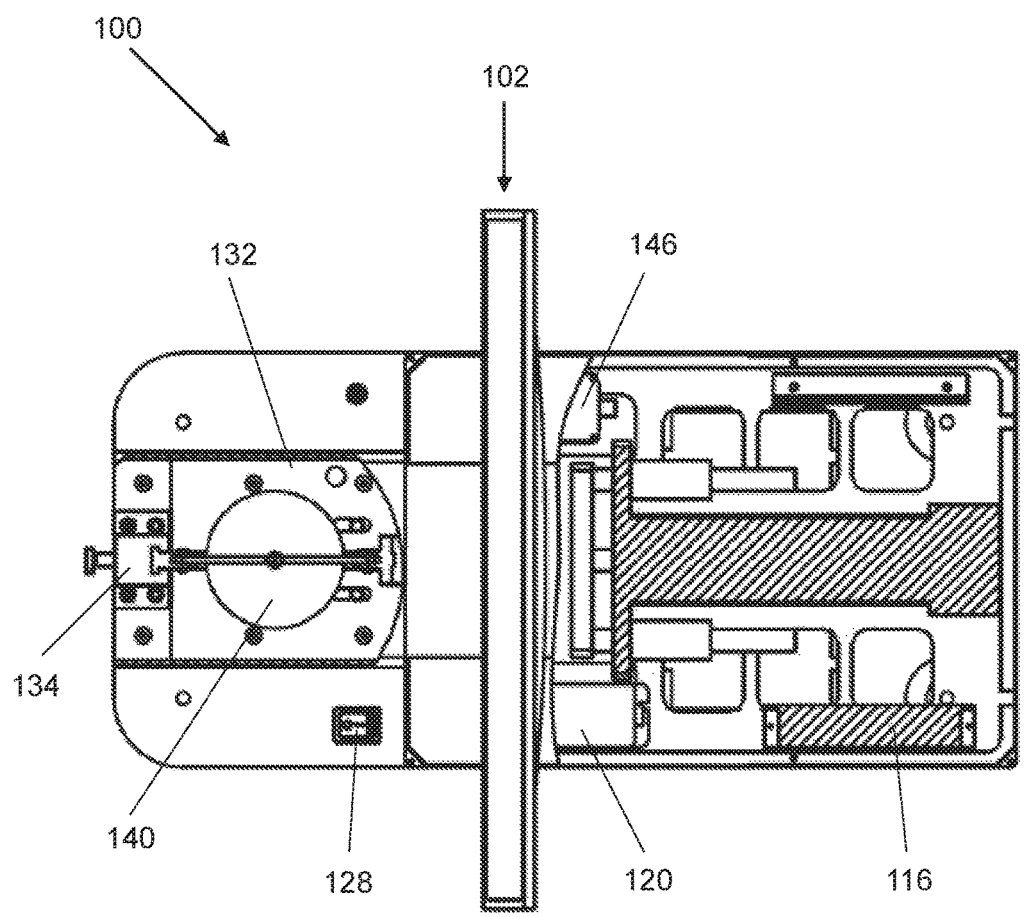
FIG. 4 illustrates a top view of the testing apparatus shown in FIG. 1, in accordance with an embodiment of the present invention.

Turning now to FIG. 2, the testing apparatus 100 provides a fixed frame 134 that is substantially stationary. The fixed frame 134 connects with a fixed pull seat 148 through the bump 150a and left connecting plate 152a. The fixed frame 134 connects a left fixed arm 154 through the bump 150a, the left connecting plate 152a and the pin 158a. The fixed arm 154 joins the connecting plate 152a at a pin 158a. The fixed arm 154 forms a terminal hook 156 that fits into the left half pull rod 190 which sits in the hole of the sample 140 when the sample is placed on the drawbar device for the testing. In this manner, the sample 140 is securely help into place on the central pull rod 166 before the testing starts.

In some embodiments, a lateral movable frame 144 is disposed in a parallel relationship with the fixed frame 134. The lateral movable frame 144 is operable to laterally advance distally and proximally in relation to the fixed frame 134 at a constant displacement rate. The lateral movable frame 144 slides along at least one guiding groove. The lateral movable frame 144 rests on a lateral movable frame adapter plate 126. The lateral movable frame 144 connects with a right lateral movable pull seat 164 through the bump 150b and right connecting plate 152b.

In one non-limiting embodiment, the lateral movable frame adapter plate 126 and the sensor adapter plate 122 are set with threads on the left and right ends, and the tension sensor 124 is mounted in the middle between the lateral movable frame adapter plate 126 and the sensor adapter plate 122. In another embodiment, the lateral movable frame 144 is connected with the front end of the tension sensor 124 through the lateral movable frame adapter plate 126, and the rear end of the tension sensor 124 is connected with the electric cylinder 112 through the sensor adapter plate 122.

In some embodiments, connecting plates 152a and 152b join the fixed frame 134 and the lateral movable frame 144. The connecting plates 152a and 152b are defined by a plurality of bumps 150. The bumps 150a, 150b are disposed at the end of the left connecting plate 152a and right connecting plate 152b. The bumps 150a and 150b also engage the fixed frame 134 and the lateral movable frame 144. The testing apparatus 100 further comprises a base plate 130 and a backing plate 132. In other embodiments, a clamping groove is operable to help retain the fixed arm 154, and the lateral movable arm 160.

The lateral movable frame 144 connects a right lateral movable arm 160 through the bump 150b, the right connecting plate 152b and the pin 158b. The lateral movable arm 160 pivotally joins the right connecting plate 152b at a pin 158b. The right lateral movable arm 160 forms a terminal hook 162 that fits into the right half pull rod 192 which is positioned in the hole of the sample 140. Through the above connection relationship, the lateral movable frame 144 drives the right lateral movable arm 160 at the constant displacement rate away from the left fixed arm 154. In this manner, the right lateral movable arm 160 and the left fixed arm 154 work to symmetrically separate the sample 140 along the axis in opposing directions.

In some embodiments, the arms 154, 160 include a hook portion that securely fits into the hole of the left half pull rod 190 and the right half pull rod 192, which form the central pull rod 166, and the sample 140 is placed on the central pull rod 166 through the hole of the sample. By means of the above connection relationship, the lateral movable frame 144 drives the right lateral movable part, whereby actually drives the lateral movable arm 160 away from the left fixed arm 154 at a constant rate, so that the arms symmetrically separate the sample 140 along an axis. The rate of separation and the tension during separation generates tension force 182 and a displacement 184 used to derive a tensile strength and the tension-displacement curve 170.

Referring to FIG. 3 again, the testing apparatus 100 further comprises a power module 118. A power switch 128 operatively connects to the power module 118. The power module is located on the lower bottom surface of the rear end of the base plate 130, and is connected with each of the electrical components by wire, and the power switch 128 is set on the base plate 130 on the right side of the working platform. In some embodiments, an electric cylinder 112 drives the lateral movable frame 144.

In review of the components: the drawbar device 142 is a frame structure that is of bilateral symmetry and can be separated in the middle; the bottom is of left and right pull seats 148 and 164, and the outer end of the pull seats is vertically set with a connecting plate 152, and the connecting plate 152 is set with bump 150, and the bumps 150a and 150b at the two ends are respectively connected to the inside the fixed frame and the lateral movable frame; the central part of the drawbar device is set with a central pull rod 166, and the central pull rod 166 can be symmetrically separated into a left half pull rod 190 and a right half pull rod 192 along the axial direction, and the left half pull rod 190 and the right half pull rod 192 are vertically welded to the left and right pull seats 148 and 164 respectively; the left fixed arm 154 and the right lateral movable arm 160 are fixed to the upper ends of the connecting plate 152 of the left and right pull seats 148 and 164 by pins 158a and 158b, and can be pivotably rotated along the pin; the inner ends of the left fixed arm 154 and the right lateral movable arm 160 are respectively connected with the left and right half pull rods 190 and 192. In one embodiment, the top of the left and right half pull rods 190 and 192 of the central pull rod 166 is set with a clamping groove, and the inner ends of the left fixed arm 154 and right lateral movable arm 160 are clamped tightly in the clamping groove.

Figure 5:
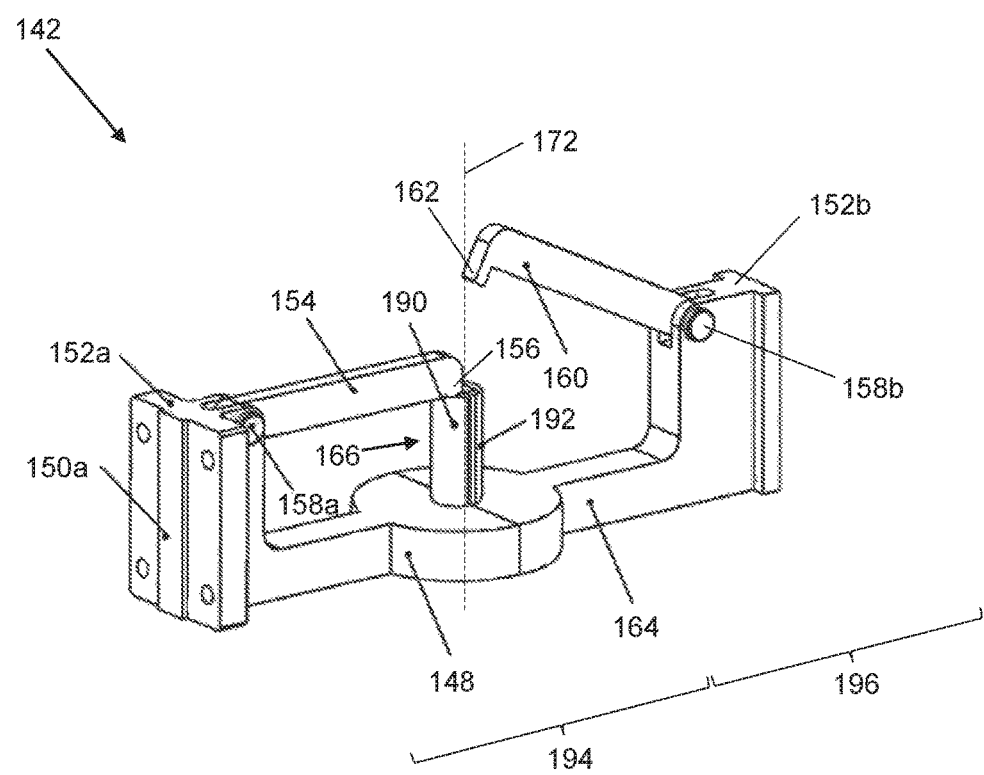
FIG. 5 illustrates a perspective view of an exemplary drawbar device, showing a left fixed part and a right lateral movable part, in accordance with an embodiment of the present invention; and Like reference numerals refer to like parts throughout the various views of the drawings.

Referring to FIG. 5, a drawbar device (142) basically has a left fixed part (194) and a right lateral movable part (196), wherein the right lateral movable part (196) being laterally movable relative to the left fixed part (194). The left fixed part (194) comprise a left fixed pull seat (148), a left connecting plate (152a), a left fixed arm (154) and a left half pull rod (190). The connecting plate (152a) is positioned at one end of the left fixed pull seat (148), and the connection plate (152a) is for connecting the left fixed part (194) with the fixed frame (134) by means of pin 150a. The left half pull rod (190) is positioned at the other end of the left fixed pull seat (148), and the fixed arm (154) is pivotably connected with the upper part of the connecting plate (152a) by means of pin (158a);

Now looking at the right side of FIG. 5, similarly, the right lateral movable part (196) comprising a right fixed pull seat (164), a connecting plate (152b), a right lateral movable arm (160) and a right half pull rod (192). The connecting plate (152b) is positioned at one end of the right lateral pull seat (164), and the connection plate (152b) is for connecting the right lateral movable part (196) with the lateral movable frame (144) by means of bump 150b. The right half pull rod (192) is positioned at the other end of the right lateral pull seat (164), and the right lateral movable arm (160) is pivotably connected with the upper part of the connecting plate (152b) by means of pin (158b).

Still on FIG. 5, the drawbar device (142) is connected with the fixed frame (134) and the lateral movable frame (144) by means of the connecting plates (152) respectively, and when the left fixed part (194) and the right lateral movable part (196) of the drawbar device (142) are being contact with each other at the half pull rod (190, 192), the left half pull rod (190) and the right half pull rod (192) are in contact as well, stick to each other and form a central pull rod (166) of the drawbar device. FIG. 5 just shows the status when the left fixed part (194) is stick and in contact with the right lateral movable part (196). So that the central pull rod (166) is able to retain a sample (140) in an upright, concentric position along an axis (172), as the sample (140) is defined by a central hole. However, FIG. 5 does not the status when the right lateral movable part (196) is pulled and separated from the left fixed part (194).

The left fixed arm (154) has a hook (156) at the other end opposite to the pin (158a), and the hook (156) is configured to be able to fit in a hole of the left half pull rod (190) of the central pull rod (166) which sits in the hole of the sample (140).

Now looking at right side of FIG. 5, similarly, the lateral movable arm (160) has a hook (162) at the other end opposite to the pin (158b), and the hook (162) is able to fit in a hole of the right half pull rod (192) of the central pull rod (160) which sits in the hole of the sample (140).

Imaging that when the lateral movable frame (144) drives the right lateral movable part (196) of the drawbar device (142) away from the left fixed part (194) of the drawbar device (142) at the constant displacement rate, the left half pull rod (190) and the right half pull rod (192) will symmetrically separate the sample (140) along the axis (172) in opposing directions.

In another embodiment, a stepper motor 110 is in operable connection with the electric cylinder 112. The stepper motor 110 drives the electric cylinder 112, and the electric cylinder 112 is in operable connection with the lateral movable frame 144 at a constant displacement rate via connection with the tension sensor 124, whereby the lateral movable frame 144 is driven by the electric cylinder 112. A stepper drive 116 is operatively connected to the stepper motor 110. In one non-limiting embodiment, the stepper motor 110 is mounted on the upper side of the electric cylinder 112, and the electric cylinder 112 is driven by the stepper motor 110. The stepper drive 116 is located on the right side of the electric cylinder 112 and is connected to the stepper motor 110 by wire for controlling the rotation speed and steering of the stepper motor 110.

In some embodiments, a tension sensor 124 detects and records a tension force on the right lateral movable arm 160 while attached to the sample 140 and moving distally from the fixed arm 154. In some embodiments, the right lateral movable frame 144 is operatively connected to the tension sensor 124 through a sensor adapter plate 122. A data acquisition module collects a tension force from the displacement sensor 138. In some embodiments, a tension signal converter 146 is operable to convert an electrical signal of the tension force 182 into a tension digital signal. The tension signal converter 146 is mounted on the base plate 130. The tension force 182 can be used to calculate and determine the tensile strength, which is the capacity of the sample 140 to withstand loads tending to elongate laterally in the direction of the lateral movable arm 144.

A displacement sensor 138 detect and records a displacement of the right lateral movable arm 160 while is attached to the sample 140 and moving distally from the fixed arm 154. One end of the displacement sensor 138 is fixed to the bottom surface of the base plate 130, and the other end is in contact with the lateral movable frame 144.

During the tension test, the data acquisition module automatically collects the displacement-tensile force data, and records the complete failure curve, and after the sample failure, the data analysis module automatically calculates the tensile strength of the material, so that the test is of high efficiency. The data acquisition module also collects a displacement from the displacement sensor 138. In some embodiments, a displacement signal converter 120 is operable to convert an electrical signal of the displacement into a displacement digital signal. The displacement signal converter 120 is mounted on the base plate 130.

A data analysis module is in operable communication with the data acquisition module. A computer program is programmable on the data analysis module to automatically calculate the tensile strength of the sample 140 based on multiple factors, namely a tensile strength constant, a sample size correction coefficient, a peak tension force, an radius of the sample 140, a radius of the inner hole of the sample 140, and a thickness of the sample 140. This can include the amount of force required by the right lateral movable arm 160 to fully, or at least partially, pull apart the sample 140.

However in another embodiment, the tensile strength is calculated from the following equation: $\sigma_t = 500\ \alpha F_{max}/(R-r)h$. For this equation, wherein $\sigma t$ is the tensile strength, 500 is a tensile strength constant, $\alpha$ is a sample size correction coefficient, $F_{max}$ is the peak tension force, R is the radius of the sample 140, r is the radius of the inner hole in the sample 140, and h is the thickness of the sample 140.

Further, the data analysis module generates a tension-displacement curve 170 diagram in real time for graphical analysis of the sample 140 (See FIG. 1). The tensile strength and the tension-displacement curve 170 diagram can be stored, exported, and manipulated to better understand the tensile strength of the soil sample 140. The tension-displacement curve diagram is based, at least partially, on the tension force and the displacement.

The testing apparatus 100 may also be provided with a computer 102 having a display screen 168 that graphically displays the tension force 182, the displacement 184, and the tension-displacement curve 170 diagram in real time. The computer is placed on the platform at the middle part of the device.

In some embodiments, the testing apparatus 100 further comprises a control board 106. The computer is also connected with the control board 106 through a data line to implement control of the device. A control board mounting seat 104 supports the control board 106. The control board mounting seat 104 is vertically mounted on the base plate 130 on the left side of the electric cylinder 112, and the control board mounting seat 104 is set up with the control board 106.

Some advantageous provided by the testing apparatus 100 include: the sample is hollow and cylindrical in shape, it is much easier and convenient to prepare the sample 140, and the sample 140 can be directly prepared by wire cutter and bench drill.

Another advantage is that the test procedure of the sample is simple and straightforward, the sample 140 can be directly mounted on the drawbar device 142 without the need for additional fixing by adhesive or clamps, and the initial structure of the sample 140 is intact. The position of the sample 140 is standardized through the central pull rod 166, and there is no eccentric stress in the process of tension. The damage effects of the sample are uniform, the fracture surface of the sample is perpendicular to the loading direction and is located in the middle of the sample.

Yet another advantage is that the universal testing machine is abandoned, and the stepper motor 110 is used to provide the tension, which saves the manufacturing cost of the instrument and reduces the volume and mass of the device. It is equipped with a displacement sensor 138 and a tension sensor that are of high precision, so that the test data is precise and reliable.

Yet another advantage is that the testing apparatus is controlled by a supporting computer program, and the software is easy to operate and easy to use. During the test, the tension-displacement curve 170 is drawn in real time, and the entire test process is clear and convenient for observation. After the test is finished, the data analysis module automatically calculates the tensile strength of the sample, and the sample parameters, test parameters and process data are automatically saved in the corresponding form files, so that the subsequent processing is convenient.

In conclusion, the testing apparatus 100 for determining tensile strength of soft rock and soil tests a sample having a central hole. A drawbar device 142 holds the sample 140 in a central, upright position. The drawbar device has two main parts, namely the left fixed part and the right lateral movable part, wherein the right lateral movable part is being lateral movable relative to the left fixed part. A fixed frame connects to the left fixed part and a lateral movable frame connects to the right lateral movable part. The drawbar device has two arms, one is the left fixed arm and another one is the right lateral movable arm, both arms have a hook portion that can fit into the central pull rod which comprises two separate half pull rods in semi cylinder shape, namely the left half pull rod and the right half pull rod. The sample is positioned on the central pull rod through the hole of the sample. An electric cylinder and stepper motor drive the right lateral movable part distally from the left fixed part to symmetrically separate the sample by separating the two half pull rods apart. A tension sensor and a displacement sensor detect the tension and displacement of the sample as the sample is pulled apart. A data acquisition module collects tension force data and displacement data. A data analysis module calculates a tensile strength based on the tension force and the displacement by the equation: $\sigma t = 500\ \alpha F_{max}/(R-r)h$, and generates a tension-displacement curve diagram, wherein $\sigma t$ is the tensile strength, 500 is a tensile strength constant, $\alpha$ is a sample size correction coefficient, $F_{max}$ is a peak tension force, R is a radius of the sample, r is a radius of the inner hole in the sample, and h is a thickness of the sample.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A testing apparatus for determining tensile strength of soft rock and soil, the apparatus comprising:
    a fixed frame and a lateral movable frame; the lateral movable frame being disposed in a parallel relationship with the fixed frame, the lateral movable frame being operable to laterally advance distally and proximally in relation to the fixed frame at a constant displacement rate;
    a stepper motor being in operable connection with the electric cylinder, and being able to drive the electric cylinder;
    an electric cylinder being in operable connection with a tension sensor, the tension sensor further being in operable connection with the lateral movable frame, whereby the lateral movable frame being able to be driven by the electric cylinder via the tension sensor at a constant displacement rate;
    a drawbar device having a left fixed part and a right lateral movable part, wherein the right lateral movable part being laterally movable relative to the left fixed part;
    the left fixed part comprising a left fixed pull seat, a left connecting plate, a left fixed arm and a left half pull rod, whereby the connecting plate is positioned at one end of the left fixed pull seat, and the connection plate is for connecting the left fixed part with the fixed frame, whereby the left half pull rod is positioned at the other end of the left fixed pull seat, whereby a fixed arm is pivotably connected with the upper part of the connecting plate by means of pin;
    similarly, the right lateral movable part comprising a right fixed pull seat, a connecting plate, a right lateral movable arm and a right half pull rod, whereby the connecting plate is positioned at one end of the right lateral pull seat, and the connection plate is for connecting the right lateral movable part with the lateral movable frame, whereby the right half pull rod is positioned at the other end of the right lateral pull seat, whereby right lateral movable arm is pivotably connected with the upper part of the connecting plate by means of pin;
    the drawbar device being connected with the fixed frame and the lateral movable frame by means of the connecting plates respectively, and when the left fixed part and the right lateral movable part of the drawbar device are being contact with each other at the half pull rod, the left half pull rod and the right half pull rod are in contact as well, stick to each other and form a central pull rod of the drawbar device, the central pull rod retaining a sample in an upright, concentric position along an axis, the sample being defined by a central hole;
    the left fixed arm having a hook at the other end opposite to the pin, whereby the hook being fitted in a hole of the left half pull rod of the central pull rod which sits in the hole of the sample;
    similarly, the lateral movable arm having a hook at the other end opposite to the pin, whereby the hook being fitted in a hole of the right half pull rod of the central pull rod which sits in the hole of the sample;
    whereby the lateral movable frame drives the right lateral movable part of the drawbar device away from the left fixed part of the drawbar device at the constant displacement rate, therefore the left half pull rod and the right half pull rod symmetrically separate the sample along the axis in opposing directions;
    a tension sensor detecting a tension generating from a lateral movable frame adapter plate which is being connection with the right lateral movable frame which is further being connection with right lateral movable part of the drawbar device while the right lateral movable part moving distally from the left fixed part;
    a displacement sensor detecting a displacement between the left fixed part and the right lateral movable part of the drawbar device while the right lateral movable part moving distally from the left fixed part;
    a data acquisition module collecting tension force data from the tension sensor, and collecting displacement data from the displacement sensor;
    a data analysis module being in operable communication with the data acquisition module, the data analysis module calculating a tensile strength of the sample based on the following factors: a tensile strength constant, a sample size correction coefficient, a peak tension force, a radius of the sample, a radius of the inner hole in the sample, and a thickness of the sample;
    the data analysis module further generating a tension-displacement curve diagram based on the tension force and the displacement;
    and a computer having a display screen graphically displaying the tension force, the displacement, and the tension-displacement curve diagram in real time.

2. The apparatus of claim 1, further comprising a case, wherein the case comprises a glass cover and a plurality of foot pads, the glass cover pivotally articulating downwardly to cover an upper part of the fixed frame and the lateral movable frame.

3. The apparatus of claim 1, wherein the lateral movable frame is operatively connected to the tension sensor through a sensor adapter plate.

4. The apparatus of claim 1, wherein the lateral movable frame rests on a lateral movable frame adapter plate.

5. The apparatus of claim 1, wherein the lateral movable frame slides along at least one guiding groove.

6. The apparatus of claim 1, further comprising a base plate and a backing plate.

7. The apparatus of claim 1, further comprising a clamping groove operable to help retain the fixed arm and the lateral movable arm.

8. The apparatus of claim 1, further comprising a tension signal converter operable to convert an electrical signal of the tension force into a tension digital signal.

9. The apparatus of claim 8, further comprising a displacement signal converter operable to convert an electrical signal of the displacement into a displacement rate digital signal.

10. The apparatus of claim 9, wherein the tension signal converter and the displacement signal converter are being mounted on the base plate.

11. The apparatus of claim 1, further comprising a power module.

12. The apparatus of claim 1, further comprising a power switch operatively connected to the power module.

13. The apparatus of claim 1, further comprising a control board and a control board mounting seat supporting the control board.

14. The apparatus of claim 1, further comprising a stepper drive being operatively connected to the stepper motor.

15. The apparatus of claim 1, wherein the data analysis module calculates the tensile strength of the sample based on the following equation: $\sigma t = 500\ \alpha F max/(R-r)h$, wherein $\sigma t$ is the tensile strength, 500 is a tensile strength constant, $\alpha$ is a sample size correction coefficient, Fmax is a peak tension force, R is a radius of the sample, r is a radius of the inner hole in the sample, and h is a thickness of the sample.

16. The apparatus of claim 1, wherein the connecting plates joining the fixed frame and the lateral movable frame, wherein the connecting plates are defined by a plurality of bumps, the bumps being disposed at opposite ends of the connecting plates, the bumps further engaging the fixed frame and the lateral movable frame.

17. The apparatus of claim 1, wherein the fixed arm and the lateral movable arm pivotally join the respective frame about at least one pin.

\* \* \* \* \*